United States Patent [19]

Daum et al.

[11] Patent Number: 4,698,350

[45] Date of Patent: Oct. 6, 1987

[54] 1-ETHYL-6-FLUORO-1,4-DIHYDRO-7-(2,6-DIMETHYL-4-PYRIDINYL)-4-OXO-3-QUINOLINECARBOXYLIC ACID AND ANTIBACTERIAL USE THEREOF

[75] Inventors: Sol J. Daum, Albany; George Y. Lesher, Schodack, both of N.Y.

[73] Assignee: Sterling Drug Inc., New York, N.Y.

[21] Appl. No.: 651,121

[22] Filed: Sep. 17, 1984

[51] Int. Cl.$^4$ .................... A61K 31/47; C07D 215/18
[52] U.S. Cl. ..................................... 514/312; 546/156
[58] Field of Search .................. 424/258; 546/156; 514/312

[56] References Cited

U.S. PATENT DOCUMENTS

| | | |
|---|---|---|
| 3,753,993 | 8/1973 | Lesher et al. . |
| 3,907,808 | 9/1975 | Lesher .............................. 424/258 |
| 4,146,719 | 3/1979 | Irikura . |
| 4,292,317 | 9/1981 | Pesson . |
| 4,533,735 | 8/1985 | Walter ............................... 546/156 |
| 4,554,352 | 11/1985 | Ranken ............................. 546/156 |

OTHER PUBLICATIONS

Albrecht–Progress in Drug Research 21, pp. 35–45, 1977.
Morrison, Organic Chemistry, 2nd Edition, pp. 824 and 825, (1970) Allyn and Bacon.

*Primary Examiner*—Robert J. Warren
*Assistant Examiner*—Robert Benson
*Attorney, Agent, or Firm*—Thomas L. Johnson; Paul E. Dupont; Robert K. Bair

[57] ABSTRACT

1-Ethyl-6-fluoro-1,4-dihydro-7-(2,6-dimethyl-4-pyridinyl)-4-oxo-3-quinolinecarboxylic acid (Win 52,522) or salt thereof, a highly potent antibacterial agent, is prepared by nitrating the corresponding 6-desfluoro compound (Win 35,439) to produce the corresponding 6-nitro compound, reducing the latter compound to produce the corresponding 6-amino compound and converting the 6-amino via its diazonium salt to said 6-fluoro compound (Win 52,522). Comparative in vitro and in vivo antibacterial test data are provided to demonstrate the uniqueness of Win 52,522 as a highly potent antibacterial agent having a broad spectrum of antimicrobial activity.

5 Claims, No Drawings

1-ETHYL-6-FLUORO-1,4-DIHYDRO-7-(2,6-DIMETHYL-4-PYRIDINYL)-4-OXO-3-QUINOLINECARBOXYLIC ACID AND ANTIBACTERIAL USE THEREOF

BACKGROUND OF THE INVENTION (1) Field of the Invention

This invention relates to a novel 7-(pyridinyl)-1-alkyl-1,4-dihydro-4-oxo-3-quinolinecarboxylic acid, salts thereof, its preparation and its antibacterial use.

(2) Information Disclosure Statement

Hepworth British Pat. No. 822,586, published October 8, 1959, shows the nitration of 1-methyl-4-quinolone-3-carboxylic acid, alternatively named 1,4-dihydro-1-methyl-4-oxo-3-quinolinecarboxylic acid, by reacting it at room temperature with a nitrating agent comprising anhydrous nitric acid together with another anhydrous mineral acid, for example, sulfuric or phosphoric acid, to produce 1-methyl-6-nitro-4-quinolone-3-carboxylic acid, alternatively named 1,4-dihydro-1-methyl-6-nitro-4-oxo-3-quinolinecarboxylic acid.

Barton et al. British Pat. No. 830,832, published Mar. 23, 1960, shows as antibacterial agents 1-alkyl-4-quinolone-3-carboxylic acids. Illustrative of compounds disclosed are 1-ethyl-6-nitro-4-quinolone-3-carboxylic acid (Example 38), which was prepared by nitrating 1-ethyl-4-quinolone-3-carboxylic acid at room temperature with a mixture of concentrated nitric acid and concentrated sulfuric acid and 1-ethyl-6-fluoro-4-quinolone-3-carboxylic acid (Example 17), alternatively named 1-ethyl-1,4-dihydro-6-fluoro-4-oxo-3-quinolinecarboxylic acid, which was prepared by heating 3-ethoxycarbonyl-6-fluoro-4-hydroxyquinoline with diethyl sulfate in aqueous sodium hydroxide solution.

Lesher and Carabateas U.S. Pat. No. 3,753,993, issued Aug. 21, 1973, shows as antibacterial agents 1-alkyl-1,4-dihydro-4-oxo-7-(pyridinyl)-3-quinolinecarboxylic acids. Illustrative of these compounds is 1-ethyl-1,4-dihydro-7-(2,6-dimethyl-4-pyridinyl)-4-oxo-3-quinolinecarboxylic acid (Example 6A, also known as Win 35,439), which was prepared stepwise as follows: first reacting 4-(3-aminophenyl)-2,6-dimethylpyridine with diethyl ethoxymethylenemalonate to produce diethyl 3-(2,6-dimethyl-4-pyridinyl)anilinomethylenemalonate (Example 6B), next heating the latter in an eutectic mixture of diphenyl and diphenyl ether (Dowtherm A) to produce ethyl 1,4-dihydro-7-(2,6-dimethyl-4-pyridinyl)-3-quinolinecarboxylate (Example 6C) and then heating said ester with ethyl iodide in dimethylformamide in the presence of anhydrous potassium carbonate to produce 1-ethyl-1,4-dihydro-7-(2,6-dimethyl-4-pyridinyl)-4-oxo-3-quinolinecarboxylic acid (Example 6A). Also shown in this patent as Example 1A is 1-ethyl-1,4-dihydro-4-oxo-7-(4-pyridinyl)-3-quinolinecarboxylic acid, now known generically as rosoxacin and also as Win 35,213.

Lesher and Carabateas U.S. Pat. No. 3,907,808, issued September 23, 1975, show as antibacterial agents 1-alkyl-1,4-dihydro-4-oxo-5(or 6)-(halo, lower-alkyl or lower-alkoxy)-7-(pyridinyl)-3-quinolinecarboxylic acids. Illustrative of these compounds is 7-(3,5-dicarboxy-2,6-dimethyl-4-pyridinyl)-1-ethyl-6-fluoro-1,4-dihydro-4-oxo-3-quinolinecarboxylic acid (Example 57A), which was prepared in six steps starting with 2-fluoro-5-nitrobenzaldehyde as follows: (1) a mixture containing 2-fluoro-5-nitrobenzaldehyde, methyl acetoacetate, methanol and concentrated ammonium hydroxide was refluxed to produce dimethyl 4-(2-fluoro-5-nitrophenyl)-1,4-dihydro-2,6-dimethyl-3,5-pyridinedicarboxylate (Example 57B); (2) oxidizing the product of Example 57B by heating it with 4 N nitric acid to produce dimethyl 4-(2-fluoro-5-nitrophenyl)-2,6-dimethyl-3,5-pyridinedicarboxylate (Example 57C); (3) catalytically hydrogenating Example 57C to produce dimethyl 4-(5-amino-2-fluorophenyl)-2,6-dimethyl-3,5-pyridinedicarboxylate (Example 57D); (4) reacting Example 57D with diethyl ethoxymethylenemalonate to produce 3-(3,5-dicarbomethoxy)-2,6-dimethyl-4-pyridinyl)-4-fluoroanilinomethylenemalonate (Example 57E); (5) heating Example 57E in Dowtherm A to produce ethyl 7-(3,5-dicarbomethoxy-2,6-dimethyl-4-pyridinyl)-6-fluoro-1,4-dihydro-4-oxo-3-quinolinecarboxylate (Example 57F); and, (6) heating Example 57F with ethyl iodide in dimethylformamide in the presence of anhydrous potassium carbonate and saponifying the resulting compound to produce 7-(3,5-dicarboxy-2,6-dimethyl-4-pyridinyl)-1-ethyl-6-fluoro-1,4-dihydro-4-oxo-3-quinolinecarboxylic acid (Example 57A). Example 56F of this patent shows the conversion of 4-(2-methoxy-5-nitrophenyl)-2,6-dimethyl-3,5-pyridinedicarboxylic acid to 4-(2-methoxy-5-nitrophenyl)-2,6-dimethylpyridine by heating it in Dowtherm A. Also, Example 64C shows the conversion of 7-(3,5-dicarboxy-2,6-dimethyl-4-pyridinyl)-1-ethyl-1,4-dihydro-6-methyl-4-oxo-3-quinolinecarboxylic acid to 7-(2,6-dimethyl-4-pyridinyl)-1-ethyl-1,4-dihydro-6-methyl-4-oxo-3-quinolinecarboxylic acid by heating it in diethyl phthalate at 240°–255° C.

T. Irikura U.S. Pat. No. 4,146,719, issued Mar. 27, 1979, shows as an antibacterial agent 1-ethyl-6-fluoro-1,4-dihydro-4-oxo-7-(1-piperazinyl)-3-quinolinecarboxylic acid, now known as norfloxacin, and its salts.

M. Pesson U.S. Pat. No. 4,292,317, issued Sept. 29, 1981, shows as antibacterial agents 6-halo-1-substituted-7-substituted-amino-1,4-dihydro-4-oxo-3-quinolinecarboxylic acids and salts thereof, including 1-ethyl-6-fluoro-1,4-dihydro-7-(4-methyl-1-piperazinyl)-4-oxo-3-quinolinecarboxylic acid, now known as pefloxacin.

SUMMARY OF THE INVENTION

In a composition of matter aspect, the invention resides in 1-ethyl-6-fluoro-1,4-dihyro-4-oxo-7-(2,6-dimethyl-4-pyridinyl)-3-quinolinecarboxylic acid of the formula I

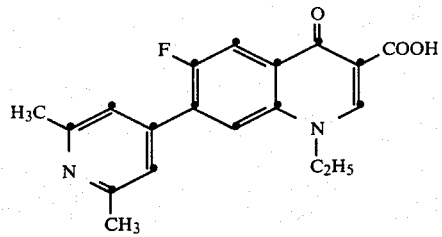

and pharmaceutically acceptable non-toxic acid-addition or cationic salts thereof. The compound of formula I and its said salts are useful as antibacterial agents, as determined by standard bacteriological evaluation procedures.

In a composition aspect, the invention resides in a composition for combatting bacteria, which comprises an antibacterially effective amount of 1-ethyl-6-fluoro-1,4-dihydro-7-(2,6-dimethyl-4-pyridinyl)-4-oxo-3- quinolinecarboxylic acid of formula I or pharmaceutically acceptable non-toxic acid-addition or cationic salt thereof together with one or more pharmaceutically acceptable vehicles or excipients.

In a method aspect, the invention resides in the method for combatting bacteria, which comprises contacting the locus of said bacteria with a composition containing the compound of formula I or pharmaceutically acceptable non-toxic acid-addition or cationic salt thereof.

In a process aspect, the invention resides in the process which comprises the steps of nitrating 1-ethyl-1,4-dihydro-7-(2,6-dimethyl-4-pyridinyl)-4-oxo-3-quinolinecarboxylic acid to produce 1-ethyl-1,4-dihydro-7-(2,6-dimethyl-4-pyridinyl)-6-nitro-4-oxo-3-quinolinecarboxylic acid, reducing said 6-nitro compound to produce 6-amino-1-ethyl-1,4-dihydro-7-(2,6-dimethyl-4-pyridinyl)-4-oxo-3-quinolinecarboxylic acid and converting said 6-amino compound via its 6-diazonium salt to produce 1-ethyl-6-fluoro-1,4-dihydro-7-(2,6-dimethyl-4-pyridinyl)-4-oxo-3-quinolinecarboxylic acid.

In another process aspect, the invention resides in the process for purifying 1-ethyl-6-fluoro-1,4-dihydro-7-(2,6-dimethyl-4-pyridinyl)-4-oxo-3-quinolinecarboxylic acid containing as impurities the corresponding 6-desfluoro and 6-hydroxy compounds which comprises converting it to its corresponding lower-alkyl 3-carboxylate, separating the ester from the reaction mixture and saponifying the ester to produce the purified acid.

DETAILED DESCRIPTION INCLUSIVE OF PREFERRED EMBODIMENTS

A preferred embodiment of the composition of matter aspect of the invention is the compound of formula I in free base form. As shown hereinbelow, this compound is a highly potent antibacterial agent having a wide spectrum of activity against a wide variety of microorganisms, including anaerobic microorganisms associated with periodontal diseases.

In the reduction step of the process aspect of the invention, the preferred reducing agent is sodium hydrosulfite in an aqueous alkaline medium.

In the conversion of the corresponding 6-amino compound to the 6-fluoro compound of formula I, the conversion is preferably carried out by first preparing the 6-diazonium chloride, reacting it with hexafluorophosphoric acid, i.e., $HPF_6$, to produce the corresponding 6-diazonium hexafluorophosphate, conveniently as its hydrofluorophosphate, and heated the latter to produce the 6-fluoro compound of formula I.

In the purification process aspect of the invention, the ethyl 3-carboxylate is formed, isolated and saponified to produce the purified compound of formula I.

The compound of formula I is useful both in the free base form and in the form of its acid-addition salt, and, both forms are within the purview of the invention. The acid-addition salt is simply an alternative form for use; and in practice, use of the salt form inherently amounts to use of the base form. The acids which can be used to prepare the acid-addition salts of the compound of formula I include preferably those which produce, when combined with the free base, pharmaceutically acceptable salts, that is, salts whose anions are relatively innocuous to the animal organism in pharmaceutical doses of the salts, so that the beneficial antibacterial properties inherent in the free base are not vitiated by side effects ascribable to the anions. Appropriate pharmaceutically acceptable salts within the scope of the invention are those derived from mineral acids such as hydrochloric acid, hydrobromic acid, sulfuric acid, phosphoric acid and sulfamic acid; and organic acids such as lactic acid, acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hyrochloride, hydrobromide, sulfate, phosphate sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said compound of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Other pharmaceutically acceptable salts of said compound of formula I are those cationic salts derived from strong inorganic or organic bases, e.g., sodium hydroxide, potassium hydroxide, trimethylammonium hydroxide, to produce the corresponding cationic salt, e.g., sodium, potassium, trimethylammonium salt, respectively.

The molecular structure of the 6-fluoro compound of formula I and corresponding intermediate 6-nitro and 6-amino compounds were assigned on the basis of evidence provided by infrared, ultraviolet, nuclear magnetic resonance and mass spectra, by the correspondence of calculated and found values for the elemental analyses, and by their method of preparation.

The manner of making and using the instant invention will now be generally described so as to enable a person skilled in the art of pharmaceutical chemistry to make and use the same.

The nitration of the known 1-ethyl-1,4-dihydro-7-(2,6-dimethyl-4-pyridinyl)-4-oxo-3-quinolinecarboxylic acid (U.S. Pat. No. 3,753,993) to produce the corresponding 6-nitro compound was carried out by reacting said known compound with concentrated nitric acid in the presence of concentrated sulfuric acid, the reaction carried out by first mixing the reactants at ambient temperature and then heating the reaction mixture at about 90° C. to 110° C., conveniently on a steam bath. The product was obtained by pouring the cooled reaction mixture into excess ice water and partially neutralizing (to a pH of about 5.5 to 6.0) the aqueous acidic solution with concentrated ammonium hydroxide and collecting the precipitated 6-nitro compound.

The conversion of 1-ethyl-1,4-dihydro-7-(2,6-dimethyl-4-pyridinyl)-6-nitro-4-oxo-3-quinolinecarboxylic acid to the corresponding 6-amino compound was conveniently carried out by heating the 6-nitro compound at about 90° C. to 110° C., conveniently on a steam bath, with sodium hydrosulfite (also named sodium dithionite) in an aqueous alkaline medium containing an organic solvent, e.g., dimethylformamide, sodium bicarbonate conveniently used to make the solution alkaline. The 6-amino compound was isolated by acidifying the cooled reaction mixture to a pH of about 5.5, preferably with acetic acid, and collecting the precipitated 6-amino compound. Alternatively, the reduction of the 6-nitro compound to the corresponding 6-amino compound can be carried out by catalytic hydrogenation using palladium-on-charcoal as catalyst and acetic acid as solvent.

The conversion of 6-amino-1-ethyl-1,4-dihydro-7-(2,6-dimethyl-4-pyridinyl)-4-oxo-3-quinolinecarboxylic acid to the corresponding 6-fluoro compound was done by first preparing the 6-diazonium salt, preferably chloride, treating its aqueous solution at about $-10°$ C. (using an ice-salt bath) with hexafluorophosphoric acid (carefully added in one portion), collecting the precipitated 6-diazonium hexafluorophosphate as its hydrohexafluorophosphate, heating the diazonium salt at about 200° C. to 240° C., preferably about 225° C. to 235° C., in a suitable solvent, e.g., paraffin oil, dissolving the cooled reaction mixture with aqueous ammonium hydroxide (e.g., 5 N), filtering the solution and slightly acidifying (to a pH of about 5.5) the filtrate with acetic acid and collecting the precipitated 6-fluoro compound (of formula I), which contained about 10–15% of the 6-desfluoro compound (produced during decomposition of the diazonium salt) and a trace of the corresponding 6-hydroxy compound. The 6-fluoro compound was separated from said impurities by converting it to its lower-alkyl, preferably ethyl, ester, separating the ester from the corresponding ester of the 6-desfluoro compound and of the 6-hydroxy compound by high pressure liquid chromatography and then saponifying the ester to produce the purified 6-fluoro acid of formula I.

The following examples will further illustrate the invention without limiting it thereto.

EXAMPLE 1

A.

1-Ethyl-1,4-dihydro-7-(2,6-dimethyl-4-pyridinyl)-6-nitro-4-oxo-3-quinolinecarboxylic Acid To a stirred solution containing 200 g. of 7-(2,6-dimethyl-4-pyridinyl)-1-ethyl-1,4-dihydro-4-oxo-3-quinolinecarboxylic acid in 440 ml of 95–98% $H_2SO_4$ was added a solution of 80 ml of 90% $HNO_3$ in 80 ml of 95–98% $H_2SO_4$ over a period of one hour. The resulting solution was stirred at room temperature for an additional 20 minutes, then heated on a steam bath for 8 hours. The reaction mixture was allowed to stand at room temperature overnight and then poured into 6000 ml of ice water. The precipitate was collected and slurried in approximately 2000 ml water. Concentrated $NH_4OH$ was added to reach a pH of 5.5–6.0. The solid was collected and washed with a small amount of ethanol and ether. Additional material was obtained by treating the original filtrate with $NH_4OH$ as described above. Recrystallization from dimethylformamide gave several crops totalling 135 g (59%) and melting from 274° C. to 298° C. A 2.8 g sample was recrystallized from 20 ml of dimethylformamide, washed with ether and dried at 120° C. for 16 hours at 0.02 mm to produce 1.54 g of 1-ethyl-1,4-dihydro-7-(2,6-dimethyl-4-pyridinyl)-6-nitro-4-oxo-3-quinolinecarboxylic acid, m.p. 289°–291° C.

B.

6-Amino-1-ethyl-1,4-dihydro-7-(2,6-dimethyl-4-pyridinyl)-4-oxo-3-quinolinecarboxylic Acid A 35 g. portion of 1-ethyl-1,4-dihydro-6-nitro-7-(2,6-dimethyl-4-pyridinyl)-4-oxo-3-quinolinecarboxylic acid was suspended in a mixture of 350 ml of hot dimethylformamide, 280 ml of saturated $NaHCO_3$ and 70 ml of water and the suspension was heated on a steam bath with stirring. A mixture of 58 g of sodium hydrosulfite in 100 ml of water was added in portions over a period of 20 minutes, during which time the reaction mixture became a clear solution and then darkened. More saturated $NaHCO_3$ solution (50 ml) was added and the reaction mixture was heated for 16 hours, after which time reduction was not complete. More sodium hydrosulfite (12 g) was added directly to the reaction mixture and heating continued for 1 hour after which time the reduction appeared to be complete (by TLC). Water (100 ml) was added, redissolving some of the material which had come out of solution; and, the mixture was heated an additional 90 minutes to insure completion of the reduction. A 1.15 g sample, m.p. 288°–290° C. with decomposition, was recrystallized from ethanol and dried for 16 hours at 130° C. under high vacuum to yield 0.9 g of 6-amino-1-ethyl-1,4-dihydro-7-(2,6-dimethyl-4-pyridinyl)-4-oxo-3-quinolinecarboxylic acid as its monohydrate, m.p. $>300°$ C.

C.

3-Carboxy-1-ethyl-1,4-dihydro-7-(2,6-dimethyl-4-pyridinyl)-4-oxo-6-quinolinyldiazonium Hexafluorophosphate A 20 g portion of 6-amino-1-ethyl-1,4-dihydro-7-(2,6-dimethyl-4-pyridinyl)-4-oxo-3-quinolinecarboxylic acid monohydrate was suspended in 100 ml of 6 N HCl and placed in an ice/salt bath. When the temperature of the mixture had reached $-10°$ C., a cold solution of 4.5 g of $NaNO_2$ in 20 ml of $H_2O$ was added in portions over a period of a few minutes. The reaction mixture was stirred for 5–10 minutes during which time it became a clear solution. Hexafluorophosphoric acid (18 ml) was carefully added in one portion whereupon a precipitate separated immediately, the temperature rising to 0° C. before dropping again. The reaction mixture was stirred for 30 minutes after addition; and, then the precipitate was collected and washed successively with water, a small volume of cold ethanol, and finally with ether. The product was vacuum-dried at 50° C. for 48 hours in the presence of $P_2O_5$ to give 29.7 g (78%) of 3-carboxy-1-ethyl-1,4-dihydro-7-(2,6-dimethyl-4-pyridinyl)-4oxo-6-quinolinyldiazonium hexafluorophosphate as its hydrohexafluorophosphate, m.p. 200°–205° C. with decomposition.

D.

1-Ethyl-6-fluoro-1,4-dihydro-7-(2,6-dimethyl-4-pyridinyl)-4-oxo-3-quinolinecarboxylic Acid A 19.6 g portion of the diazonium salt of Example 3 was placed in a 3-necked round bottom flask equipped with a mechanical stirrer and connected to a nitrogen apparatus. Paraffin oil (200 ml) was added, the apparatus evacuated and filled with nitrogen. The reaction vessel was then immersed in an oil bath preheated to 230° C. After 10 minutes the starting material gummed up and formed a ball, making stirring difficult. After heating for a total of 25 minutes the hot oil was decanted and the reaction mixture allowed to cool. It was then washed with n-hexane, broken up with a pestle and dissolved in 5 N $NH_4OH$ (approximately 900 ml). This solution was filtered through a pad of diatomaceous earth and the filtrate acidified to a pH of 5.5 with concentrated acetic acid. After being refrigerated overnight, the precipitate (the 6-fluoro compound) was collected and found to contain a trace of the corresponding 6-hydroxy compound (evidence MS) and 10–15% of the correspondng 6-desfluoro compound (evidence NMR). Recrystallization from dimethylformamide yielded a first crop of 4.4 g (43%) and a second crop of 1.5 g (15%). Products from several runs were combined and after two recrystallizations from DMF still contained approximately 10% of the 6-desfluoro compound. This compound was ultimately purified (Example 2) by converting it to the ethyl ester, separating it from the 6-desfluoro ethyl ester by high pressure liquid chromatography, then saponifying it back to the acid.

EXAMPLE 2

A. Ethyl 1-Ethyl-6-fluoro-1,4-dihydro-7-(2,6-dimethyl-4-pyridinyl)-4-oxo-3-quinolinecarboxylate A 12.3 g sample of the 6-fluoro compound containing about 10% of the 6-desfluoro compound (i.e., the final product of Example 1D) and another 12.2 g of the same 6-fluoro compound obtained from mother liquors of other runs and of varying purity were converted to 14.8 g of ethyl ester by refluxing for 48 hours in 1N ethanolic HCl containing a small quantity of triethyl orthoformate to take up any traces of water present (In a typical example 600 ml 1N ethanolic HCl and 3 ml triethyl orthoformate were used for 5.0 g of fluoro acid). The 14.8 g of ester was purified by preparative HPLC using a solvent system of 60% acetone/40% hexane to give 8.3 g of pure 6-fluoro ester, i.e., ethyl 1-ethyl-6-fluoro-1,4-dihydro-7-(2,6-dimethyl-4-pyridinyl)-4-oxo-3-quinolinecarboxylate, which was used directly in the next step (Example 2B).

B. 1-Ethyl-6-fluoro-1,4-dihydro-7-(2,6-dimethyl-4-pyridinyl)-4-oxo-3-quinolinecarboxylic Acid To 8.39 of the ethyl ester of Example 2A was added 200 ml of water and 1.8 g of sodium hydroxide. The mixture was heated on a steam bath for 3 and ½ hours, after which hydrolysis was incomplete. NaOH (0.9 g) was added and heating continued for 16 hours. The hot reaction mixture was filtered and the filtrate allowed to cool, after which it was acifified to a pH of 5–5.5 with concentrated acetic acid. The precipitate was collected and washed successively with water, ethanol and ether. The product was recrystallized from dimethylformamide to yield 6.7 g (88%) of 1-ethyl-6-fluoro-1,4-dihydro-7-(2,6-dimethyl-4-pyridinyl)-4-oxo-3-qunolinecarboxylic acid, m.p. >300° C.

The usefulness of 1-ethyl-6-fluoro-1,4-dihydro-7-(2,6-dimethyl-4-pyridinyl)-4-oxo-3-quinolinecarboxylic acid (compound of formula I and of Example 2B which is designated hereinbelow as Win 52,522) and its uniqueness as a highly potent antibacterial agent having a broad spectrum of antimicrobial activity have been demonstrated by the following experiments.

EXPERIMENT 1

Comparative in Vitro Antibacterial Activity of Win 52,522, Win 35,439, Methicillin and Vancomycin As noted above, Win 52,522 is the compound of formula I, i.e., the compound of Example 2B hereinabove. Win 35,439 is its 6-desfluoro analog. Methicillin, used as its sodium salt (THE MERCK INDEX, 10th Ed., 5842), is 6-(2,6-dimethoxybenzamido)penicillanic acid sodium salt. Vancomycin, used as its hydrochloride (THE MERCK INDEX, 10th Ed., 9731), is an amphoteric glycopeptide antibiotic.

Summary

Win 52,522 (MIC values $\leq 0.008$ to 0.5 mcg/ml) was 2–8 times more potent in vitro than Win 35,439 against several Gram-positive cocci, including S. aureus, S. epidermidis and Streptococcus species. Win 52,522 was 32 to >8000 times more potent, and 16 to 125 times more potent, in vitro than methicillin and vancomycin, respectively, against the Staphylococcus species. Win 52,522 was 2 to 8 times less potent than methicillin against S. pyogenes and S. pneumoniae, but was 32 to >500 times more potent than methicillin against S. faecalis. Win 52,522 was bactericidal (MBC/MIC $\leq 4$) for all 39 bacterial test strains.

Introduction

This study was designed to determine the comparative in vitro antibacterial activity of Win 52,522, Win 35,439, methicillin and vancomycin against strains of Staphylococcus and Streptococcus. Escherichia coli and Pseudomonas aeruginosa test strains were also examined to illustrate the Gram-negative potency of Win 52,522 relative to that of Win 35,439.

Compound Preparation

Win 52,522 and Win 35,439 were solubilized in 0.1 ml of 0.5 N NaOH/mg of compound and diluted in sterile distilled water to 160 mcg/ml. Vancomycin and methicillin were solubilized in sterile distilled water to 1250 mcg/ml of base compound. The stock solutions were sterilized by filtration through membrane filters with a 0.45 μm pore size.

Media

Mueller-Hinton broth (MHB) - BBL
Mueller-Hinton agar (MHA) - BBL
Brain Heart Infusion (BHI) broth - Difco
Brain Heart Infusion (BHI) agar - Difco
Normal horse serum (NHS) - Gibco

Bacterial Cultures

The bacterial cultures listed in Table I (hereinbelow) were grown overnight at 37° C. in MHB for all cultures except the Streptococcus strains. These were grown in BHI+10% NHS. The overnight broth cultures were adjusted to an optical density of 0.10 (650 nm, B L Spectronic 20) in sterile distilled water and subsequently diluted to $6.7 \times 10^6$ cells/ml in MHB or BHI+1% NHS.

Minimal Inhibitory Concentration (MIC) Test

Serial two-fold dilutions of the compound solutions were prepared in MHB (or in BHI+1% NHS for tests with Streptococci) and dispensed into 96-well microtiter trays in a volume of 0.1 ml/well using a Sandy Springs (Bellco Glass Co.) dispenser. The trays were then inoculated with 0.0015 ml of a suspension containing $6.7 \times 10^6$ cells/ml of the appropriate inoculum using a MIC-2000 inoculator (Dynatech Corp.) resulting in a final inoculum of approximately $1 \times 10^4$ cells/well or $1 \times 10^5$ cells/ml. The trays were incubated at 37° C. for 18–20 hours and the minimal inhibitory concentration (MIC), defined as the lowest concentration of compound to inhibit visible bacterial growth, was recorded.

Minimal Bactericidal Concentration (MBC) Test

After the MIC values were recorded, the contents in the microtiter trays were thoroughly mixed on a Bellco Mini-orbital Shaker (Bellco Glass Co.) for 3 min. at a setting of 8. A portion (0.0015 ml) from each well was then transferred via an MIC-2000 inoculator to plates containing MHA or BHI agar+10% NHS. The plates were incubated at 37° C. for 18–20 hrs. The minimal bactericidal concentration (MBC), defined as the lowest concentration of compound that prevented the formation of a recognizable colony on the agar surface, was recorded.

Results and Discussion

The individual test results are shown in Table I and in summary form in Table II.

TABLE I

IN VITRO ANTIBACTERIAL ACTIVITY OF WIN 52,522, WIN 35,439, METHICILLIN AND VANCOMYCIN

MIC AND MBC VALUES IN mcg/ml

| Bacteria | WIN 52,522 MIC | WIN 52,522 MBC | WIN 35,439 MIC | WIN 35,439 MBC | METHICILLIN MIC | METHICILLIN MBC | VANCOMYCIN MIC | VANCOMYCIN MBC |
|---|---|---|---|---|---|---|---|---|
| S. aureus 13-8-A | 0.03 | 0.03 | 0.06 | 0.125 | 1 | 2 | 0.5 | 0.5 |
| S. aureus 4-81 | 0.015 | 0.03 | 0.06 | 0.125 | 2 | 2 | 0.5 | 0.5 |
| S. aureus 24-81 | 0.015 | 0.03 | 0.06 | 0.125 | 1 | 2 | 0.5 | 0.5 |
| S. aureus 34-81 | 0.03 | 0.03 | 0.06 | 0.06 | 1 | 2 | 0.5 | 0.5 |
| S. aureus 41-81 | 0.015 | 0.015 | 0.06 | 0.25 | 1 | 1 | 1 | 1 |
| S. aureus 21-81A | 0.015 | 0.015 | 0.06 | 0.125 | 1 | 1 | 0.5 | 1 |
| S. aureus S-234 | 0.015 | 0.03 | 0.06 | 0.125 | 8 | 32 | 1 | 1 |
| S. aureus S-500 | 0.03 | 0.06 | 0.125 | 0.25 | 8 | 32 | 1 | 1 |
| S. aureus 10-81 | 0.03 | 0.03 | 0.125 | 0.125 | 8 | 16 | 1 | 1 |
| S. aureus 59-81 | 0.015 | 0.03 | 0.125 | 0.25 | 32 | 64 | 1 | 1 |
| S. aureus 39881 | 0.015 | 0.03 | 0.06 | 0.06 | 125 | >125 | 1 | 1 |
| S. aureus Smith | 0.03 | 0.03 | 0.125 | 0.125 | 1 | 1 | 1 | 1 |
| S. aureus (25923)* | 0.015 | 0.03 | 0.125 | 0.125 | 2 | 2 | 1 | 1 |
| S. aureus Giorgio | <0.008 | 0.015 | 0.03 | 0.125 | 2 | 4 | 1 | 1 |
| S. aureus VA16951 | 0.015 | 0.015 | 0.06 | 0.06 | 4 | 8 | 1 | 1 |
| S. epidermidis (12228)* | 0.06 | 0.06 | 0.25 | 0.25 | 4 | 4 | 1 | 1 |
| S. epidermidis (17917)* (ATCC No. 17917) | 0.06 | 0.125 | 0.5 | 0.5 | 4 | 4 | 1 | 1 |
| S. epidermidis 1-3-H (ATCC No. 17917) | 0.06 | 0.06 | 0.25 | 0.25 | 2 | 4 | 1 | 1 |
| S. epidermidis 1-5-H (ATCC No. 17917) | 0.06 | 0.06 | 0.25 | 0.25 | 1 | 2 | 2 | 2 |
| S. epidermidis 2-1-B (ATCC No. 17917) | 0.03 | 0.03 | 0.25 | 0.25 | 1 | 2 | 1 | 2 |
| S. pyogenes C203 | 0.5 | 0.5 | 4 | >16 | 0.125 | 0.125 | 16 | 16 |
| S. pyogenes (89)** | 0.5 | 0.5 | 4 | >16 | ≦0.06 | ≦0.06 | 16 | 16 |
| S. pyogenes 7948-15 | 0.5 | 0.5 | 4 | >16 | 0.25 | 0.125 | 16 | 16 |
| S. pneumoniae Type I | 0.25 | 0.25 | 2 | 2 | ≦0.06 | ≦0.06 | 16 | 16 |
| S. pneumoniae Type III | 0.5 | 0.5 | 4 | 4 | 0.125 | 0.125 | ≦0.06 | 16 |
| S. faecalis (11700)* | 0.25 | 0.25 | 1 | 1 | 64 | 64 | 1 | >125 |
| S. faecalis 4510 | 0.125 | 0.125 | 0.5 | 0.5 | 64 | 64 | 2 | >125 |
| S. faecalis (8043)* | 0.25 | 0.5 | 1 | 2 | >125 | >125 | 1 | >125 |
| S. enterococcus 0-2-13 | 0.25 | 0.25 | 2 | 2 | 8 | 8 | 0.25 | 16 |
| E. coli Vogel | 0.25 | 0.5 | 2 | 2 | | | | |
| E. coli 198 | 0.5 | 0.5 | 2 | 2 | | | | |
| E. coli (8739)* | 0.25 | 0.25 | 0.5 | 0.5 | | | | |
| E. coli AH719 | 0.25 | 0.25 | 0.5 | 0.5 | | | | |
| E. coli 2350 | 0.25 | 0.25 | 0.5 | 0.5 | | | | |
| P. aeruginosa MGH-2 | 16 | 16 | 8 | 16 | | | | |
| P. aeruginosa (7700)* | 16 | 16 | 16 | >16 | | | | |
| P. aeruginosa (15442)* | 16 | 16 | >16 | >16 | | | | |
| P. aeruginosa (9027)* | 4 | 16 | 8 | >16 | | | | |
| P. aeruginosa (27853)* | 16 | 16 | 16 | >16 | | | | |

*ATCC No.
**SWRI No.

TABLE II

Inhibitory (MIC) and Bactericidal (MBC) Values

| Bacteria (No. Tested) | Compound | MIC (mcg/ml) 50% | MIC (mcg/ml) 90% | MIC (mcg/ml) Range | MBC (mcg/ml) 50% | MBC (mcg/ml) 90% | MBC (mcg/ml) Range |
|---|---|---|---|---|---|---|---|
| S. aureus (15) | Win 52,522 | 0.015 | 0.03 | ≦0.008–0.03 | 0.03 | 0.03 | 0.015–0.06 |
| | Win 35,439 | 0.06 | 0.125 | 0.03–0.125 | 0.25 | 0.5 | 0.125–0.5 |
| | Methicillin | 2 | 8 | 1–125 | 4 | >64 | 2–>64 |
| | Vancomycin | 1 | 1 | 0.5–1 | 1 | 1 | 0.5–1 |
| S. edidermidis (5) | Win 52,522 | 0.06 | 0.06 | 0.03–0.06 | 0.06 | 0.06 | 0.03–0.125 |
| | Win 35,439 | 0.25 | 0.25 | 0.25–0.5 | 0.25 | 0.25 | 0.25–0.5 |
| | Methicillin | 2 | 4 | 1–4 | 4 | 4 | 2–4 |
| | Vancomycin | 1 | 1 | 1–2 | 1 | 2 | 1–2 |
| Streptococcus sp. (9) | Win 52,522 | 0.25 | 0.5 | 0.125–0.5 | 0.5 | 0.5 | 0.125–0.5 |
| | Win 35,439 | 2 | 4 | 0.5–4 | 2 | >16 | 0.5–>16 |
| | Methicillin | 0.25 | 64 | ≦0.06–>125 | 0.125 | 64 | ≦0.06–>125 |
| | Vancomycin | 2 | 16 | ≦0.06–16 | 16 | >125 | 16–>125 |
| E. coli (5) | Win 52,522 | 0.25 | 0.25 | 0.25–0.5 | 0.25 | 0.5 | 0.25–0.5 |
| | Win 35,439 | 0.5 | 2 | 0.5–2 | 0.5 | 2 | 0.5–2 |
| P. aeruginosa (5) | Win 52,522 | 16 | 16 | 4–16 | 16 | 16 | 16 |

TABLE II-continued

| | | Inhibitory (MIC) and Bactericidal (MBC) Values | | | | | |
|---|---|---|---|---|---|---|---|
| | | MIC (mcg/ml) | | | MBC (mcg/ml) | | |
| Bacteria (No. Tested) | Compound | 50% | 90% | Range | 50% | 90% | Range |
| | Win 35,439 | 16 | 16 | 8->16 | >16 | >16 | 16->16 |

From Table I it can be seen that Win 52,522 was bactericidal for all the Gram-positive and Gram-negative test strains (MBC/MIC≦4). Win 35,439 was bacteriostatic against the 3 strains of S. pyogenes. Although less potent than Win 52,522, methicillin was also bactericidal for the Gram-positive cocci, while vancomycin was bacteriostatic for one strain of S. pneumoniae and all 4 strains of S. faecalis.

Relative to Win 35,439, Win 52,522 was 2 to 8 times more potent in vitro against the Gram-positive cocci and E. coli, and similarly potent against P. aeruginosa. These results are consistent with in vivo mouse protection tests where Win 52,522 was 3.6 (s.c.) to 3.9 (p.o.) times more efficacious than Win 35,439 against an S. aureus, and 2.6 (s.c.) to 2.0 (p.o.) times more efficacious against an E coli infection (Experiment 3 hereinbelow).

Win 52,522 was 32 to >8000 times more potent in vitro than methicillin against the Staphylococcus species, 32 to >500 times more potent than methicillin against S. faecalis, but was 2 to 8 times less potent than methicillin against S. pyogenes and S. pneumoniae.

Win 52,522 was 16 to 125 times more potent in vitro than vancomycin against the Gram-positive cocci with two exceptions: (1) Win 52,522 was 8 times less potent than vancomycin against S. pneumoniae type III and, (2) was equal in potency against the one enterococcus (strain 0-2-B) tested.

The in vitro test results here support the results from an in vivo test showing Win 52,522 to be 16 and >91 times more efficacious than vancomycin and methicillin, respectively, against a methicillin-resistant Staphylococcus aureus infection in mice.

From the in vitro results reported here and the in vivo results shown hereinbelow (Experiment 3), it follows that Win 52,522 should be even more effective than vancomycin in killing deep-seated staphylococcal tissue infections. Vancomycin is an alternate drug of choice for penicillinase-producing S. aureus [The Choice of Antimicrobial Drugs, Medical Letter, Mar. 5, 1982] and the drug of choice for the treatment of methicillin resistant Staphylococcus aureus [Methicillin-resistant Staphylococcus aureus. United States Morbidity and Mortality Weekly Report, Nov. 20, 1981, Vol. 30, No. 45, 557].

EXPERIMENT 2

Antimicrobial Activity of Win 52,522, Win 35,439, Rosoxacin, Norfloxacin, Perfloxacin and Tetracycline against Anaerobic and Microaerophilic Bacterial Associated with Oral Infections

Summary

Win 52,522 was found to have high activity against all thirteen of the target anaerobic microorganisms and compared favorably with tetracycline, the current antibiotic of choice.

Introduction

It is generally accepted that certain microorganisms are the primary etiologic agents in the initiation of periodontal diseases [Socransky et al., Present Status of Studies on the Microbial Etiology of Periondontal Diseases, pp. 1-14. In: R. Genco and S. Mergenhagen (Ed.), Host-Parasite Interactions in Periodontal Diseases, 1982, Amer. Soc. Micro. Washington, DC.] Furthermore, there is increasing evidence to support the hypothesis that specific microorganisms are associated with each of the various forms of periodontal disease [Socransky et al., supra]. Accordingly, the rationale has been advanced for the use of antimicrobials in the prevention, control and treatment of these pandemic diseases. There is evidence in various animal models that the administration of various antibiotics can reduce the clinical signs of gingivitis and also decrease the progression of alveolar bone loss associated with aggressive periodontal diseases [Gibson, Antibiotics and Periodontal Disease: A Selective Review, J. Amer. Dent. Assoc. 104, 213-218 (1982)]. In man, the data would also appear supportive of the argument that antimicrobial agents are extremely useful in treating established disease, particularly when used to augment conventional therapies [Gibson, supra]. In this regard, the antibiotics tetracycline and metronidazole have been shown to be particularly useful [Genco, Antibiotics in the Treatment of Human Periodotal Diseases J. Periodontol. 52, 545-558 (1981)]; however, these agents do not appear to be ideal since they are not active against all the microorganisms considered to participate in the disease process. Furthermore, there are an increasing number of reports indicating that many of the so-called primary pathogens of periodontal disease have already evidenced patterns of increased tolerance to these agents [Gibson, supra, Genco, supra and Williams et al., Subgingival Microflora of Periodontal Patients On Tetracycline Therapy J. Clin. Periodontol. 6, 210-215 (1979)]. Hence, there exists an important and timely need to discover and develop new antimicrobial agents which will have utility in the prevention/management of periodontal diseases. The studies described herein show that Win 52,522 was found to be extremely active against a number of anaerobic microorganisms associated with periodontal diseases.

Microorganisms

The microorganisms used in these studies are listed in Table A hereinbelow.

Culture Conditions

1. Maintenance. Prior to use, all strains were maintained in the lyophilized state. During the study, cultures were examined on blood agar basal medium supplemented with 5.0% (v/v) defibrinated rabbit blood. Culture transfer was accomplished weekly with all cultures being incubated in an anaerobic atmosphere (GasPak jar; BBL).

2. Agar Medium. The basal test medium consisted of trypticase soy agar (40 g), yeast extract (1 g), glucose (2 g) and 960 ml of distilled water pH 7.2. [Mashimo et al., J. Clin. Micro. 17, 187-191 (1983)]. Subsequent to sterilization and cooling to 50° C., the medium was supplemented with 4% (v/v) defibrinated rabbit blood and 0.5 μg/ml menadione (Vitamin K₃) The agent under evaluation was also added at this time to the concentration desired. Subsequent to pouring of the plates, they were permitted to dry at 4° C. for 24 hr.

3. Determination of Agent MIC. The minimal inhibitory concentration (MIC) of the various test agents was determined using an agar dilution technique. Agents and appropriate reference compounds were added to achieve a series of concentrations ranging between 32 µg/ml and 0.007 µg/ml. The inocula were prepared from 96-hr. cultures grown on the maintenance medium. Subsequent to a purity evaluation, colonies were removed and suspended in trypticase soy broth supplemented with 5 µg/ml menadione and 2% lysed rabbit blood filtrate to achieve an $OD_{650}$ of 0.1 (this corresponded to approximately $10^8$ cells/ml). Cultures were inoculated aerobically on the modified trypticase soy blood agar plates by use of a Steer's replicator (which delivers about $10^5$ cells per spot). The plates were allowed to dry for a time not exceeding 30 min. and then incubated at 37° C. under an atmosphere of 80% $N_2$, 10% $H_2$ and 5% $CO_2$ maintained in an anaerobic chamber (Coy Manufacturing Co.) for 48 hr. The MIC was defined as the lowest concentration completely inhibiting growth.

Agents

Tetracycline stock solutions (1 mg/ml) were made subsequent to dissolution in water. Stock solutions (1 mg/ml) of the remaining test compounds were made subsequent to dissolution in 1/10 N NaOH. Appropriate controls indicated at the levels used NaOH did not affect the viability of the test microorganisms.

Results

The antimicrobial activities of the compounds tested are shown in Table A.

TABLE A

SUSCEPTIBILITY OF SELECTED ANAEROBIC MICROORGANISMS TO TEST COMPOUNDS

| | Win Number µg/ml | | | | | |
|---|---|---|---|---|---|---|
| MICROORGANISMS | 35,213[a] | 35,439[b] | 52,522[c] | 9,424[d] | 50,297[e] | 50,150[f] |
| F. polymorphum | >10 | 4 | 0.5 | 0.12 | >10 | 8 |
| A. viscosus | >10 | 8 | 1.0 | 2.0 | >10 | >10 |
| B. melaninogenicus | 8 | 8 | 1.0 | 0.5 | 4.0 | 4 |
| Capnocytophaga suptigena | 1 | 0.5 | 0.06 | 1.0 | 0.5 | 0.25 |
| B. intermedius | 0.5 | 0.25 | 0.06 | 2.0 | 0.5 | 0.5 |
| Eikenella corrodens | 8 | 2.0 | 0.5 | 2.0 | 4.0 | 4.0 |
| B. oralis | >10 | >10 | 4.0 | 0.12 | 4.0 | 4.0 |
| B. gingivalis | >10 | >10 | 2.0 | 0.12 | 4.0 | 4.0 |
| A. actinomycetemcomitans | 0.12 | 0.25 | 0.12 | 1.0 | 0.06 | 0.06 |
| B. fragilis | >10 | >10 | 4.0 | 1.0 | >10 | 8.00 |
| F. nucleatum | >10 | 4 | 0.5 | 0.75 | 8.00 | 8.00 |
| Wolinella recta | 0.5 | 0.5 | 0.12 | — | 0.12 | 0.25 |
| Campylobacter sputorum | >10 | >10 | 8.0 | — | 2.0 | 4.0 |

[a]Rosoxacin
[b]6-Desfluoro analog of Win 52,522
[c]Applicants Example 2B
[d]Tetracycline
[e]Norfloxacin
[f]Pefloxacin Win 52,522 is seen to be markedly superior to both Win 35,213 and 35,439. In fact, Win 52,522 showed a broad spectrum of antimicrobial activity, comparing favorably with the currant antibiotic of choice, tetracycline. Wins 50,297 and 50,150 were less active.

EXPERIMENT 3

In Vivo Antibacterial Activity of Win 52,522 Compared to Win 35,439 Against *Staphylococcus aureus* and *Escherichia Coli* Infections in Mice

SUMMARY

Win 52,522 was determined to be more efficacious than Win 35,439, by either subcutaneous and oral routes of medication, against infections in mice produced by penicillin-sensitive and methicillin-resistant *Staphylococcus aureus* strains.

MATERIALS AND METHODS

Animals

ICR mice, female, 18–20 grams each.

Antibacterial Agents

Win 52,522, Win 35,439, methicillin (Win 9,410) and vancomycin (Win 39,556).

Bacterial Cultures

*Escherichia coli* Vogel
*Staphylococcus aureus* 39881
*Staphylococcus aureus* Smith

Culture Media

Brain Heart Infusion Agar (Difco)
Brain Heart Infusion Broth (Difco)

Gastric Mucin

Bacteriological grade, Lot No. 0617, ICN Pharmaceuticals, Inc. A 5% (w/v) suspension was prepared by adding 25 grams of gastric mucin to 475 ml of cold tap water. The suspension was mixed for 20–30 minutes with an Omni-mixer, stored at 4° C. overnight and just before use brought to pH 7.2 with 40% (w/v) NaOH.

Preparation of Antimicrobial Drug Solutions

Solutions of Win 52,522 and Win 35,439 were prepared by dissolving the appropriate weight of drug in 0.3 to 0.4 ml of 1 N NaOH and then bringing the solutions to the desired volume with distilled water. Methicillin and vancomycin were dissolved directly in distilled water.

Preparation of Bacterial Cultures

A *Staphylococcus aureus* Smith

Two and one-half ml of pool were added to 247.5 ml of 5% gastric mucin to provide the test inoculum containing $2.1 \times 10^4$ cells/ml.

B. *Staphylococcus aureus* 39881

The culture was streaked onto three Brain Heart Infusion Agar plates and incubated 16 hours at 37° C. The cells were washed off each plate with five ml of saline and the cell suspension was shaken with glass beads for two minutes on a paint shaker. The suspension was diluted with saline so that a 1:00 dilution gave a 44% T reading on a B+L Spectronic 20 (650 nm) calibrated with saline. The stock suspension was diluted 1:24 (10 ml stock suspension + 230 ml 5% mucin) to obtain the test inoculum containing $1.55 \times 10^9$ cells/ml.

C. *Escherichia coli* Vogel

The culture was inoculated into 10 ml of Brain Heart Infusion broth and grown statically for 16 hours at 37° C. Fresh tubes of the same broth were inoculated with 0.1 ml portions of the 16 hour broth culture and incubation continued for 5 hours at 37° C. The 5 hour broth culture was finally diluted with saline to provide the test inoculum containing $4.0 \times 10^7$ cells/ml.

Infection of Mice

Mice were inoculated intraperitoneally with 0.5 ml of the bacterial test inoculum.

Medication of Mice

A. *Staphylococcus aureus* Smith

1. Single dose test—Mice were medicated subcutaneously or orally once (0.5 ml) one-half hour postinfection.

2. Multiple dose test—Mice were medicated subcutaneously (0.2 ml) or orally (0.5 ml) at the following times: six hours and one hour preinfection (infection at 2 pm) and twice a day (8 a.m. and 3:30 p.m.) for the next two successive days.

B. *Staphylococcus aureus* 39881

Mice were medicated twice: at one-half and four hours postinfection. The drugs were administered by both subcutaneous (0.2 ml) and oral (0.5 ml) routes.

C. *Escherichia coli* Vogel

Mice were medicated subcutaneously or orally once (0.5 ml) one-half hour postinfection.

Deaths were recorded daily for seven days for all tests. Fifty percent protective dose values ($PD_{50}$'s) were calculated using probit analysis [SAS Users Guide: Statistics, 1982 Edition, SAS Institute, Inc., Cary, N.C.].

Results

The in vivo antibacterial activity of Win 52,522, as compared to Win 35,439, against a *Staphylococcus aureus* Smith infection in mice is shown in Tables 1 and 2.

TABLE 1

In Vivo Antibacterial Activity of Win 52,522 and Win 35,439 Against a *Staphylococcus aureus* Smith Infection in Mice - Single Dose Test

| Drug | Dose (mg/kg) | Route | Survivors/ Total | Protective Dose 50% (mg/kg) (95% Confidence Limits) |
|---|---|---|---|---|
| Win 52,522 | 0.095 | sc | 0/10 | 0.8(0.6–1.1) |
|  | 0.19 |  | 0/10 |  |
|  | 0.39 |  | 2/10 |  |
|  | 0.78 |  | 4/10 |  |
|  | 1.56 |  | 10/10 |  |
| Win 35,439 | 0.78 | sc | 1/10 | 2.9(2.3–4.3) |
|  | 1.56 |  | 0/10 |  |
|  | 3.13 |  | 6/10 |  |
|  | 6.25 |  | 10/10 |  |
| Win 52,522 | 0.19 | po | 0/10 | 1.4* |
|  | 0.39 |  | 0/10 |  |
|  | 0.78 |  | 0/10 |  |
|  | 1.56 |  | 7/10 |  |
|  | 3.13 |  | 10/10 |  |
| Win 35,439 | 0.39 | po | 0/10 | 5.5* |
|  | 0.78 |  | 1/10 |  |
|  | 1.56 |  | 0/10 |  |
|  | 3.13 |  | 0/10 |  |
|  | 6.25 |  | 7/10 |  |
| Vancomycin | 0.78 | sc | 2/10 | 1.1(0.6–1.5) |
|  | 1.56 |  | 9/10 |  |
|  | 3.13 |  | 9/10 |  |
|  | 6.25 |  | 10/10 |  |
|  | 12.5 |  | 10/10 |  |
| Infected Controls |  | — | 0/20 |  |

*Estimate

TABLE 2

In Vivo Antibacterial Activity of Win 52,522 and Win 35,439 Against a *Staphylococcus aureus* Smith Infection in Mice - Multiple Dose Test

| Drug | Dose (mg/kg) | Route | Survivors/ Total | Protective Dose 50% (mg/kg) (95% Confidence Limits) |
|---|---|---|---|---|
| Win 52,522 | 0.19 | sc | 0/10 | 1.8(1.3–2.4) |
|  | 0.39 |  | 0/10 |  |
|  | 0.78 |  | 0/10 |  |
|  | 1.56 |  | 4/10 |  |
|  | 3.13 |  | 9/10 |  |
|  | 6.25 |  | 10/10 |  |
|  | 12.5 |  | 10/10 |  |
| Win 35,439 | 3.13 | sc | 1/10 | 7.1(5.4–10.2) |
|  | 6.25 |  | 3/10 |  |
|  | 12.5 |  | 10/10 |  |
|  | 25 |  | 10/10 |  |
| Win 52,522 | 0.19 | po | 0/10 | 2.1(1.6–2.7) |
|  | 0.39 |  | 0/10 |  |
|  | 0.78 |  | 0/10 |  |
|  | 1.56 |  | 2/10 |  |
|  | 3.13 |  | 9/10 |  |
|  | 6.25 |  | 10/10 |  |
|  | 12.5 |  | 10/10 |  |
| Win 35,439 | 3.13 | po | 0/10 | 7.2(5.4–9.6) |
|  | 6.25 |  | 4/10 |  |
|  | 12.5 |  | 9/10 |  |
|  | 25 |  | 10/10 |  |
| Infected Controls | — | — | 0/20 |  |

Win 52,522 was 3.6 (sc) and 3.9 (po) times more efficacious than Win 35,439 when administered as a single dose one-half hour postinfection. Win 52,522 was 3.9 (sc) and 3.4 (po) times more efficious than Win 35,439 against the same infection when given in a multiple dose regimen. $PD_{50}$ values with Win 52,522 against a methicilin-resistant *Staphylococcus aureus* infection in mice were 1.1 and 1.6 mg/kg for subcutaneous and oral medication, respectively, as shown in Table 3.

TABLE 3

In Vivo Antibacterial Activity of Win 52,522, Win 35,439, Methicillin and Vancomycin Against a *Staphylococcus aureus* 39881 (Methicillin-resistant) Infection in Mice

| Drug | Dose (mg/kg) | Route | Survivors/ Total | Protective Dose 50% (mg/kg) (95% Confidence Limits) |
|---|---|---|---|---|
| Win 52,522 | 0.19 | sc | 0/10 | 1.1(0.1–4.1) |
|  | 0.39 |  | 0/10 |  |
|  | 0.78 |  | 2/10 |  |
|  | 1.56 |  | 10/10 |  |
|  | 3.13 |  | 9/10 |  |
|  | 6.25 |  | 10/10 |  |
| Win 35,439 | 1.56 | sc | 0/10 | 4.9* |
|  | 3.13 |  | 0/10 |  |
|  | 6.25 |  | 9/10 |  |
|  | 12.5 |  | 7/10 |  |
| Win 52,522 | 0.19 | po | 0/10 | 1.6(1.3–2.4) |
|  | 0.39 |  | 0/10 |  |
|  | 0.78 |  | 1/10 |  |
|  | 1.56 |  | 4/10 |  |
|  | 3.13 |  | 10/10 |  |
|  | 6.25 |  | 10/10 |  |
| Win 35,439 | 1.56 | po | 1/10 | 7.2(5.6–10.0) |
|  | 3.13 |  | 0/10 |  |
|  | 6.25 |  | 3/10 |  |
|  | 12.5 |  | 10/10 |  |
| Methicillin | 25 | sc | 0/10 | >100 |
|  | 50 |  | 0/10 |  |
|  | 100 |  | 0/10 |  |
| Vancomycin | 6.25 | sc | 0/10 | 17.7(13.8–22.6) |
|  | 12.5 |  | 1/10 |  |
|  | 25 |  | 9/10 |  |
|  | 50 |  | 10/10 |  |
| Infected Controls | — | — | 0/20 |  |

*Estimate
**Two doses - one-half and four hours postinfection

Win 52,522 (sc) was 4.5 and 16 times more active against that infection than Win 35,439 and vancomycin, respectively.

The in vivo activity of Win 52,522 and 35,439 against an *Escherichia coli* Vogel infection in mice is shown in Table 4.

TABLE 4

In Vivo Antibacterial Activity of Win 52,522 and Win 35,439 Against a *Escherichia coli* Vogel Infection in Mice

| Drug | Dose (mg/kg) | Route | Survivors/ Total | Protective Dose 50% (mg/kg) (95% Confidence Limits) |
|---|---|---|---|---|
| Win 52,522 | 1.56 | sc | 0/10 | 5.2* |
|  | 3.13 |  | 0/10 |  |
|  | 6.25 |  | 8/10 |  |
|  | 12.5 |  | 10/10 |  |
|  | 25 |  | 10/10 |  |
| Win 35,439 | 3.13 | sc | 1/10 | 13.5(10.5–19.2) |
|  | 6.25 |  | 0/10 |  |
|  | 12.5 |  | 4/10 |  |
|  | 25 |  | 10/10 |  |
| Win 52,522 | 1.56 | po | 0/10 | 8.2(6.3–10.8) |
|  | 3.13 |  | 0/10 |  |
|  | 6.25 |  | 2/10 |  |
|  | 12.5 |  | 9/10 |  |
|  | 25 |  | 10/10 |  |
| Win 35,439 | 3.13 | po | 0/10 | 16.5(12.6–21.8) |
|  | 6.25 |  | 0/10 |  |
|  | 12.5 |  | 2/10 |  |
|  | 25 |  | 9/10 |  |
| Infected Controls | — | — | 0/20 |  |

*Estimate

Subcutaneous and oral PD$_{50}$ values of Win 52,522 against that infection were 5.2 and 8.2 mg/kg., approximately one-half those of Win 35,439.

The results of this study demonstrate that Win 52,522, by both parenteral and oral medication routes, is a very potent antibacterial agent against infections in mice produced by both penicillin-sensitive and methicillin-resistant *Staphylococcus aureus* strains.

The compound of formula I or a pharmaceutically-acceptable non-toxic acid-addition or cationic salt thereof can be prepared for use by conventional pharmaceutical procedures: that is, by dissolving or suspending them in a pharmaceutically acceptable vehicle, e.g., water, aqueous alcohol; glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

We claim:

1. 1-Ethyl-6-fluoro-1,4-dihydro-7-(2,6-dimethyl-4-pyridinyl)-4-oxo-3-quinolinecarboxylic acid of the formula

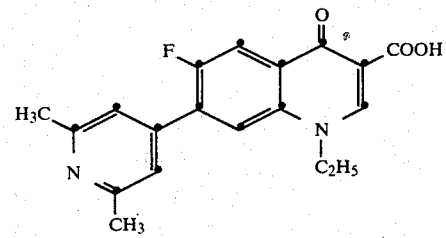

and pharmaceutically acceptable non-toxic acid-addition or cationic salts thereof.

2. 1-Ethyl-6-fluoro-1,4-dihydro-7-(2,6-dimethyl-4-pyridinyl)-4-oxo-3-quinolinecarboxylic acid.

3. A composition for combatting bacteria which comprises an antibacterially effective amount of 1-ethyl-6-fluoro-1,4-dihydro-7-(2,6-dimethyl-4-pyridinyl)-4-oxo-3-quinolinecarboxylic acid or pharmaceutically acceptable non-toxic acid-addition or cationic salt thereof together with one or more pharmaceutically acceptable vehicles or excipients.

4. A composition according to claim 3 containing 1-ethyl-6-fluoro-1,4-dihydro-7-(2,6-dimethyl-4-pyridinyl)-4-oxo-3-quinolinecarboxylic acid.

5. A method for combatting bacteria, which comprises contacting the locus of said bacteria with a composition according to 3.

* * * * *

UNITED STATES PATENT AND TRADEMARK OFFICE
CERTIFICATE OF CORRECTION

PATENT NO.   :   4,698,350

DATED        :   October 6, 1987

INVENTOR(S)  :   Sol J. Daum and George Y. Lesher

It is certified that error appears in the above-identified patent and that said Letters Patent is hereby corrected as shown below:

Cover page, column 2, "Robert J. Warren" should read --Robert J. Warden--.

Column 1, line 52, after "produce" insert: --ethyl 1-ethyl-1,4-dihydro-7-(2,6-dimethyl-4-pyridinyl)-4-oxo-3-quinolinecarboxylate and hydrolyzing said ester to produce--.

Columns 9 and 10, Table II, "S. edidermidis" should read --S. epidermidis--.

Column 11, line 56, "Bacterial" should read --Bacteria--.

Column 17, line 7, Table 3, in heading, "Dose" should read --Dose**--.

Signed and Sealed this

Sixteenth Day of August, 1988

Attest:

DONALD J. QUIGG

Attesting Officer

Commissioner of Patents and Trademarks